United States Patent [19]

Armstrong

[11] 4,018,889
[45] Apr. 19, 1977

[54] OXYTETRACYCLINE COMPOSITIONS

[75] Inventor: William W. Armstrong, Mill Neck, N.Y.

[73] Assignee: Pfizer Inc., New York, N.Y.

[22] Filed: Jan. 2, 1976

[21] Appl. No.: 646,295

[52] U.S. Cl. .................................. 424/80; 424/227
[51] Int. Cl.$^2$ ................. A61K 31/79; A61K 31/65
[58] Field of Search ...................... 424/227; 424/80

[56] References Cited

UNITED STATES PATENTS

| | | | |
|---|---|---|---|
| 2,980,584 | 4/1961 | Hammer | 424/227 |
| 2,987,437 | 6/1961 | Hessel | 424/227 |
| 2,990,331 | 6/1961 | Neumann et al. | 424/227 |
| 3,557,280 | 1/1971 | Weber et al. | 424/80 |
| 3,957,972 | 5/1976 | Weber et al. | 424/80 |

FOREIGN PATENTS OR APPLICATIONS

| | | | |
|---|---|---|---|
| 825,656 | 1975 | Belgium | 424/227 |
| 2,258,187 | 1/1975 | France | 424/227 |
| 1,091,287 | 4/1961 | Germany | 424/80 |
| 805,026 | 2/1957 | United Kingdom | 424/80 |
| 802,111 | 9/1956 | United Kingdom | 424/80 |

OTHER PUBLICATIONS

Japanese Patent Application Publication No. SHO 47-303, (Jan. 6, 1972).
Japanese Patent Application Publication No. SHO 43-1758, (Jan. 22, 1968).
E. H. Gans & T. Higuchi, J. Pharm. Sci; 46, p. 458 (1957).

*Primary Examiner*—Albert T. Meyers
*Assistant Examiner*—Daren M. Stephens
*Attorney, Agent, or Firm*—Francis X. Murphy; Charles J. Knuth; Allen J. Spiegel

[57] ABSTRACT

Oxytetracycline aqueous solutions containing 2-pyrrolidone as a co-solvent suitable for pharmaceutical use and especially useful for either oral, topical or parenteral administration are disclosed.

8 Claims, No Drawings

OXYTETRACYCLINE COMPOSITIONS

BACKGROUND OF THE INVENTION

This invention relates to antibiotic compositions suitable for pharmaceutical use. More particularly, it relates to aqueous oxytetracycline solutions containing 2-pyrrolidone.

Previous efforts made to prepare compositions suitable for topical or parenteral administration which contain more than 200 mg./ml. have been unsuccessful. This is of particular importance in the case of veterinary oxytetracycline parenteral compositions in which high doses are required.

U.S. Pat. No. 2,980,584 discloses aqueous parenteral solutions of oxytetracycline metal complexes containing 25–80% of an acetic or lactic acid carboxamide, such as N,N-dimethylacetamide and N-($\beta$-hydroxyethyl) lactamide at a pH of 8.5–9.5. Concentrations of 10 to 100 mg./ml. are disclosed.

U.S. Pat. No. 2,990,331 discloses parenteral solutions of oxytetracycline hydrochloride, containing about 50 mg./ml. having a pH value between 5 and 7, containing magnesium ions, an alkali bisulfite and a carboxylic acid amide, such as lactic acidhydroxyethyl amide.

U.S. Pat. No. 3,557,280 discloses aqueous solutions of oxytetracycline containing 1 to 20% oxytetracycline, a magnesium compound and polyvinylpyrrolidone, 7.5 to 25%, at a pH of 8.0 to 9.5.

Belgian Pat. No. 825,656 discloses aqueous solutions of oxytetracycline containing 4 to 11% oxytetracycline, 20 to 30% of a polyethylene glycol, such as polyethylene glycol 400, a magnesium compound and 0.10 to 0.35% of a buffer, such as tris-(hydroxymethyl)-aminomethane at a pH of 8 to 9.

French Pat. Publication No. 2,258,187 discloses aqueous solutions of oxytetracycline containing 50 mg./ml. of oxytetracycline, 5 to 7.49% polyvinylpyrrolidone and up to 24.9% of an acid amide containing one to six carbon atoms, such as dimethylacetamide, at a pH of 8 to 9.5.

SUMMARY OF THE INVENTION

It has now been found that stable high potency solutions of oxytetracycline can be provided by means of a novel pharmaceutical composition comprising a solution in water of from about 1 to 40% by weight of an antibiotic compound selected from oxytetracycline and the pharmaceutically acceptable acid addition salts thereof, about 0.8 to 1.3 molar proportion of a pharmaceutically acceptable magnesium compound soluble in said solution, and from about 10 to 50% by weight of 2-pyrrolidone, said composition having a pH value in the range of from about 7.5 to 9.5.

DETAILED DESCRIPTION OF THE INVENTION

Oxytetracycline, the therapeutically-active component of this invention, is a widely used tetracycline-type antibiotic. It is particularly described in U.S. Pat. No. 2,516,080. An effective concentration range for oxytetracycline in the solutions of this invention is generally from about 1 to 40% by weight of the total in the form of the free base or a pharmaceutically acceptable acid addition salt. The preferred form is the free base with the preferred concentration being from about 10 to 40% by weight, with the especially preferred concentration being from about 20 to 30% by weight.

Examples of suitable oxytetracycline acid addition salts which can be used include such pharmaceutically acceptable acid addition salts as the hydrochloride, hydrobromide, sulfate, nitrate, ascorbate, citrate, gluconate, lactate, isonicotinate, gentisinate, pantothenate, salicylate, glucuronate, formate and glutamate. However, the preferred acid addition salt is oxytetracycline hydrochloride.

Magnesium ions combine with oxytetracycline in solution to form magnesium-oxytetracycline chelates. Magnesium oxide is a convenient and preferred source of magnesium ions, but other magnesium compounds useful for the purpose of this invention include magnesium chloride, magnesium acetate, magnesium sulfate, magnesium ascorbate, magnesium lactate and magnesium gluconate. The molar ratio of magnesium to oxytetracycline in these compositions is about from 0.8 to 1.3 mole of oxytetracycline. This ratio is necessary to produce clear stable solutions. Suspended solids remain in the solvent when introduction of less than 0.8 or more than 1.3 moles of magnesium ion is used.

2-Pyrrolidone is present as a co-solvent in a concentration of from about 10 to 50% based on the total weight of the composition. 2-Pyrrolidone is also known as 2-pyrrolidinone, 2-oxopyrrolidine, $\alpha$-pyrrolidone and 2-ketopyrrolidine. It has an ordal $LD_{50}$ of 8 gm/kg in rats and 3.8 gm/kg by intraperitoneal injection in mice. Its use allows for minimum volume per dose and excellent syringeability due to low viscosity of the resultant composition.

As an optional ingredient polyvinylpyrrolidone having a molecular weight of between about 5,000 and 100,000 (K-12 to 30) may also be present in a concentration of from about 1 to 7% by weight. The polyvinylpyrrolidone preferred for this invention is one having an average molecular weight of about 10,000 – 17,000 (where K—value = 17). It is also present in part as a cosolubilizer and may improve tissue toleration.

The stability of these solutions for therapeutic administration is still further enchanced by the use of antioxidants such as sodium or magnesium formaldehyde sulfoxylate at levels of from about 0.01 to 1.0% by weight.

The pH value is adjusted if necessary to pH 7.5 to 9.5. The preferred range is pH 8.5 to 9.0. The pH can be adjusted with organic bases such as aminoethanol, dimethlaminoethanol, dimethylamine and so forth. Of these compounds, aminoethanol is the preferred compound.

The compositions of this invention are readily prepared by mixing the magnesium compound with the 2-pyrrolidone and water at about 75° C and slowly adding the oxytetracycline antibiotic with stirring until dissolved. The pH is then adjusted to the desired range. If polyvinylpyrrolidone is to be included it is added to the 2-pyrrolidone and water before the addition of the magnesium compound as previously described.

Oxytetracycline is currently available for parenteral administration at a concentration of 50 mg./ml. Therefore a 500 Kg steer would require 200 ml. of a 50 mg./ml. product injected into 5 to 10 different areas in order to receive an effective dose. The compositions of this invention obviate this difficulty in that easily syringable high dosage compositions are now possible, e.g. 200 mg./ml.

These compositions are also easy to syringe over a wide temperature range, have acceptable animal tissue toleration, give therapeutic blood levels and are satisfactory from a physical and chemical stability standpoint.

The primary application is as a veterinary parenteral composition but they can also be used for topical application.

EXAMPLE 1

|  | gm/100 ml. |
|---|---|
| Oxytetracycline (based on a potency of 927 γ/mg. plus a 5% overage) | 22.65 |
| Magnesium oxide | 1.921 |
| 2-Pyrrolidone | 40.00 |
| Magnesium formaldehyde sulfoxylate | 0.44 |
| 2-Aminoethanol | 0.10 |
| Water q.s. to | 100 ml. |

The 2-pyrrolidone was mixed with the water. The solution was heated to about 75° C and the magnesium formaldehyde sulfoxylate was added and dissolved with stirring. The magnesium oxide was then slurried with the solution. The oxytetracycline was slowly added with stirring until a clear solution resulted. The solution was allowed to cool to room temperature and the pH adjusted to 8.5 with 2-aminoethanol. The solution was then brought up to volume with water.

The above solution containing 200 mg./ml. of oxytetracycline activity had a viscosity of 13.0 cts. at 25° C.

Tissue toleration was acceptable and blood levels were satisfactory after subcutaneous injection in cattle.

The substitution of 1.0 gm. of sodium formaldehyde sulfoxylate for the magnesium formaldehyde sulfoxylate produced a product similar to the above.

EXAMPLE 2

|  | mg./100 ml. |
|---|---|
| Oxytetracycline (based on a potency of 927 γ/mg. plus a 5% overage) | 22.65 |
| Magnesium oxide | 1.921 |
| 2-Pyrrolidone | 40.00 |
| Polyvinylpyrrolidone,K-17 | 5.00 |
| Magnesium formaldehyde sulfoxylate | 0.44 |
| 2-Aminoethanol | 0.17 |
| Water q.s. to | 100 ml. |

The 2-pyrrolidone was mixed with water. Polyvinylpyrrolidone was then added and stirred until dissolved. The procedure as described in Example 1 was then followed.

The resulting product, containing 200 mg./ml. of oxytetracycline activity, had a viscosity of 23 cts. at 25° C.

Tissue toleration was acceptable and blood levels satisfactory after subcutaneous and intramuscular injection in cattle.

The substitution of 1.0 gm. of sodium formaldehye sulfoxylate for the magnesium formaldehyde sulfoxylate produced a product similar to the above.

EXAMPLE 3

The following solution containing 25 mg./ml. of oxytetracycline activity was prepared using the procedure described in Example 1.

|  | gm./100 ml. |
|---|---|
| Oxytetracycline (based on a potency of 927 γ/mg. plus a 5% overage) | 2.831 |
| Magnesium oxide | 0.245 |
| 2-Pyrrolidone | 10.00 |
| Sodium formaldehyde sulfoxylate | 1.00 |
| 2-Aminoethanol | 0.012 |

-continued

|  | gm./100 ml. |
|---|---|
| Water q.s. to | 100 ml. |

The viscosity was 2 cts. at 25° C.

EXAMPLE 4

The following solution containing 50 mg./ml. of oxytetracycline activity was prepared using the procedure described in Example 1.

|  | gm./100 ml. |
|---|---|
| Oxytetracycline (based on a potency of 927 γ/mg. plus a 5% overage) | 5.662 |
| Magnesium oxide | 0.490 |
| 2-Pyrrolidone | 20.00 |
| Sodium formaldehyde sulfoxylate | 1.00 |
| 2-Aminoethanol | 0.065 |
| Water q.s. to | 100 ml. |

The viscosity was 2.5 cts. at 25° C.

EXAMPLE 5

A solution containing 100 mg./ml. of oxytetracycline activity was prepared using the procedure described in Example 1.

|  | gm./100 ml. |
|---|---|
| Oxytetracycline (based on a potency of 927 γ/mg. plus a 5% overage) | 11.325 |
| Magnesium oxide | 0.480 |
| 2-Pyrrolidone | 35.00 |
| Sodium formaldehyde sulfoxylate | 1.00 |
| Water q.s. to | 100 ml. |

The viscosity was 3.0 cts. at 25° C.

EXAMPLE 6

The following solution containing 200 mg./ml. of oxytetracycline activity was prepared using the procedure described in Example 2.

|  | gm./100 ml. |
|---|---|
| Oxytetracycline (based on a potency of 927 γ/mg. plus a 5% overage) | 22.65 |
| Magnesium oxide | 1.421 |
| 2-Pyrrolidone | 40.00 |
| Polyvinylpyrrolidone,K-30 | 5.00 |
| Magnesium formaldehyde sulfoxylate | 0.44 |
| 2-Aminoethanol | 0.50 |
| Water q.s. to | 100 ml. |

The viscosity was 5.0 cts. at 25° C.

EXAMPLE 7

A solution containing 200 mg./ml. of oxytetracycline activity was prepared using the procedure described in Example 2.

|  | gm./100 ml. |
|---|---|
| Oxytetracycline hydrochloride (based on a potency of 905 γ/mg. plus a 5% overage) | 23.20 |
| Magnesium oxide | 1.921 |
| 2-Pyrrolidone | 40.00 |
| Polyvinylpyrrolidone,K-17 | 5.00 |
| Magnesium formaldehyde sulfoxylate | 0.44 |
| 2-Aminoethanol | 3.84 |

|  | gm./100 ml. |
|---|---|
| Water q.s. to | 100 ml. |
| The viscosity was 45 cts. at 25° C. | |

EXAMPLE 8

A solution containing 200 mg./ml. of oxytetracycline activity was prepared using the procedure described in Example 2.

|  | gm./100 ml. |
|---|---|
| Oxytetracycline (based on a potency of 927 γ/mg. plus a 5% overage) | 22.65 |
| Magnesium chloride, hexahydrate | 9.668 |
| 2-Pyrrolidone | 40.00 |
| Polyvinylpyrrolidone,K-17 | 5.00 |
| Magnesium formaldehyde sulfoxylate | 0.44 |
| 2-Aminoethanol | 0.88 |
| Water q.s. to | 100 ml. |
| The viscosity was 35 cts. at 25° C. | |

The viscosity was 35 cts. at 25° C.

EXAMPLE 9

The following solution containing 200 mg./ml. of oxytetracycline activity was prepared using the procedure described in Example 1.

|  | gm./100 ml. |
|---|---|
| Oxytetracycline (based on a potency of 927 γ/mg. plus a 5% overage) | 22.65 |
| Magnesium acetate, tetrahydrate | 10.021 |
| 2-Pyrrolidone | 40.00 |
| Sodium formaldehyde sulfoxylate | 1.00 |
| 2-Aminoethanol | 0.76 |
| Water q.s. to | 100 ml. |
| The viscosity was 33 cts. at 25° C. | |

EXAMPLE 10

A solution containing 300 mg./ml. of oxytetracycline activity was prepared using the procedure described in Example 1.

|  | gm./100 ml. |
|---|---|
| Oxytetracycline (based on a potency of 927 γ/mg. plus a 5% overage) | 33.975 |
| Magnesium oxide | 2.94 |
| 2-Pyrrolidone | 50.00 |
| Sodium formaldehyde sulfoxylate | 1.00 |
| Water q.s. to | 100 ml. |
| The viscosity was 70 cts. at 25° C. | |

EXAMPLE 11

A solution containing 350 mg./ml. of oxytetracycline activity was prepared using the procedure described in Example 1.

|  | gm./100 ml. |
|---|---|
| Oxytetracycline (based on a potency of 927 γ/mg. plus a 5% overage) | 39.597 |
| Magnesium oxide | 3.43 |
| 2-Pyrrolidone | 50.00 |
| Sodium formaldehyde sulfoxylate | 1.00 |
| Water q.s. to | 100 ml. |
| The viscosity was 200 cts. at 25° C. | |

EXAMPLE 12

A solution containing 400 mg./ml. of oxytetracycline activity was prepared using the procedure described in Example 1.

|  | gm./100 ml. |
|---|---|
| Oxytetracycline (based on a potency of 927 γ/mg. plus a 5% overage) | 45.30 |
| Magnesium oxide | 3.92 |
| 2-Pyrrolidone | 50.00 |
| Sodium formaldehyde sulfoxylate | 1.00 |
| Water q.s. to | 100 ml. |
| The viscosity was 785 cts. at 25° C. | |

What is claimed is:

1. An oxytetracycline composition comprising a solution in water of from about 1 to 40% by weight of an antibiotic compound selected from the group consisting of oxytetracycline and the pharmaceutically acceptable acid addition salts thereof, from about 0.8 to 1.3 molar proportion of a pharmaceutically acceptable magnesium compound soluble in said solution, and from about 10 to 50% by weight of 2-pyrrolidone, said composition having a pH value in the range of from about 7.5 to 9.5.

2. A composition as claimed in claim 1 wherein said antibiotic compound is oxytetracycline.

3. A composition as claimed in claim 1 wherein said magnesium compound is introduced in the form of magnesium oxide.

4. A composition of Claim 1 wherein polyvinylpyrrolidone having an average molecular weight of between about 5,000 and 100,000 is also present in a concentration of from about 1 to 7% by weight of the total.

5. A composition as claimed in claim 1 wherein said antibiotic compound is present at a level of from about 10 to 40% by weight.

6. A composition as claimed in claim 1 wherein said antibiotic compound is present at a level of from about 20 to 30% by weight.

7. A composition as claimed in claim 1 having a pH value of from about 8.5 to 9.

8. An oxytetracycline composition comprising a solution in water of from about 20 to 30% by weight of oxytetracycline, from about 0.8 to 1.3 molar proportion of a pharmaceutically acceptable magnesium compound soluble in said solution, from about 10 to 50% by weight of 2-pyrrolidone and from about 1 to 7% by weight of polyvinylpyrrolidone, said composition having a pH value in the range of from about 8.5 to 9.

* * * * *

UNITED STATES PATENT AND TRADEMARK OFFICE
CERTIFICATE OF CORRECTION

PATENT NO. : 4,018,889
DATED : April 19, 1977
INVENTOR(S) : William W. Armstrong It is certified that error appears in the above-identified patent and that said Letters Patent are hereby corrected as shown below:

Col. 2, line 26, "ordal" should read --oral--.

Col. 3, line 34, "mg./100 ml." should read --gm./100 ml.--.

Signed and Sealed this

Tenth Day of April 1979

[SEAL]

Attest:

RUTH C. MASON
Attesting Officer

DONALD W. BANNER
Commissioner of Patents and Trademarks